(12) United States Patent
Ogier-Denis et al.

(10) Patent No.: US 9,217,156 B2
(45) Date of Patent: Dec. 22, 2015

(54) NON HUMAN ANIMAL MODEL FOR ULCERATIVE COLITIS AND ITS MAIN COMPLICATIONS

(75) Inventors: Eric Ogier-Denis, Paris (FR); Xavier Treton, Paris (FR); Fanny Daniel, Paris (FR); Cecile Guichard, Paris (FR); Eric Pedruzzi, Paris (FR); Yoram Bouhnik, Paris (FR); Yann Harnoy, Paris (FR)

(73) Assignee: Institut National de la Sante et de la Recherche Medicale (INSERM), Paris (FR)

( * ) Notice: Subject to any disclaimer, the term of this patent is extended or adjusted under 35 U.S.C. 154(b) by 103 days.

(21) Appl. No.: 14/118,001

(22) PCT Filed: Apr. 13, 2012

(86) PCT No.: PCT/IB2012/000882
§ 371 (c)(1),
(2), (4) Date: Nov. 15, 2013

(87) PCT Pub. No.: WO2012/140516
PCT Pub. Date: Oct. 18, 2012

(65) Prior Publication Data
US 2014/0373186 A1 Dec. 18, 2014

(51) Int. Cl.
*C12N 15/85* (2006.01)
*A01K 67/027* (2006.01)
*A01K 67/02* (2006.01)
*A61K 49/00* (2006.01)
*A61K 31/155* (2006.01)
*A61K 31/429* (2006.01)
*A61K 31/47* (2006.01)
*C12Q 1/68* (2006.01)

(52) U.S. Cl.
CPC ............ *C12N 15/8509* (2013.01); *A01K 67/02* (2013.01); *A01K 67/0276* (2013.01); *A61K 31/155* (2013.01); *A61K 31/429* (2013.01); *A61K 31/47* (2013.01); *A61K 49/0008* (2013.01); *C12Q 1/6876* (2013.01); *A01K 2227/10* (2013.01); *A01K 2227/105* (2013.01); *A01K 2267/03* (2013.01); *A01K 2267/0325* (2013.01); *C12N 2015/8527* (2013.01)

(58) Field of Classification Search
CPC .............. A01K 2267/03; A01K 67/02; C12N 15/8509; A61K 31/155
See application file for complete search history.

(56) References Cited

PUBLICATIONS

Kuwano et al. (Free Radical Biology & Medicine. 2008; 45: 1642-1652).*
Shelley Jane Edmunds, PhD Dissertation, 2010. "The Effects of Kiwifruit Extracts on Gene and Protein Expression Levels in in vitro and in vivo mouse models of inflammatory bowel disease" The University of Auckland. pp. 1-278.*
Kuwano et al., "Tumor necrosis factor alpha activates transcription of the NADPH oxidase organizer 1 (NOXO1) gene and upregulates superoxide production in colon epithelial cells", Free Radical Biology and Medicine, Dec. 15, 2008, pp. 1642-1652, vol. 45, No. 12, Elsevier Science, US.
Kanneganti et al., "Animal models of colitis-associated carcinogenesis", J Biomed Biotechnol, 2011, pp. 1-23.
Sasaki et al., "Receptor activator of nuclear factor-kappaB ligand-induced mouse osteoclast differentiation is associated with switching between NADPH oxidase homologues", Free Radical Biology and Medicine, Jul. 15, 2009, pp. 189-199, vol. 47, No. 2, Elsevier Science, US.
Mai et al., "Interleukin 10 inhibits interferon I and tumor necrosis factor I+-stimulated activation of NADPH oxidase 1 in human colonic epithelial cells and the mouse colon", Journal of Gastroenterology, Aug. 28, 2009, pp. 1172-1184, vol. 44, No. 22.
Kuhn et al, "Interleukin-10-deficient mice develop chronic enterocolitis", Cell, 1993, pp. 263-274, vol. 75.
Otter et al., "Identification of Urinary Biomarkers of Colon Inflammation in IL10 (-/-) Mice Using Short-Column LCMS Metabolomics", Journal of Biomedicine & Biotechnology, 2011.
Coant et al., "NADPH oxidase 1 modulates WNT and NOTCH signaling to control the fate of proliferative progenitor cells in the colon", Mol Cell Biol, 2010, pp. 2636-2650, vol. 30.
Dammanahalli et al., "Genetic interleukin-10 deficiency causes vascular remodeling via the upregulation of Nox1", Journal of Hypertension, Nov. 2011, pp. 1-17.

* cited by examiner

*Primary Examiner* — Scott Long
(74) *Attorney, Agent, or Firm* — Whitham, Curtis, Christofferson & Cook PC; Michael Whitham; Whitney Fields

(57) ABSTRACT

The present invention relates to a non human model animal for ulcerative colitis and its main complications such as primary sclerosing cholangitis and colorectal cancer. More particularly, the present invention relates to a transgenic non human animal model for ulcerative colitis and its main complications such as primary sclerosing cholangitis, and colorectal cancer comprising a targeted disruption in the IL10 and NOX1 genes so that IL10 and NOX1 are not expressed in said animal.

6 Claims, No Drawings

NON HUMAN ANIMAL MODEL FOR ULCERATIVE COLITIS AND ITS MAIN COMPLICATIONS

CROSS REFERENCE TO RELATED APPLICATIONS

This application is a National Stage Application based on the International Application No. PCT/IB2012/000882 filed Apr. 13, 2012 which claims priority to European Application 1162272 filed Apr. 13, 2011.

FIELD OF THE INVENTION

The present invention relates to a non human model animal for ulcerative colitis and its main complications such as primary sclerosing cholangitis and colorectal cancer.

BACKGROUND OF THE INVENTION

Ulcerative colitis (UC) is a chronic intermittent and relapsing inflammatory bowel disease (IBD) of the colon characterized by superficial mucosal lesions that extend through the rectum and progress upstream. The natural history of UC is characterized by the progression of colonic lesions in up to 50% of subjects. This suggests that the colonic mucosa has a "global" susceptibility to environmental factors, but etiology of UC remains unknown and current treatments are limited as 30% of patients require colectomy. Human studies identified unbalanced endoplasmic reticulum stress (ERS) in unaffected colonic mucosa from UC patients[1,2]. Animal models in which ERS is disrupted are highly sensitive to chemically-induced colitis [2-6] or develop intestinal inflammation [2,7-9] suggesting that unbalanced ERS give rise to inflammation. However, there are no ERS-regulating strategies proposed in the management of UC in part by the lack of adequate experimental model mimicking UC.

SUMMARY OF THE INVENTION

The present invention relates to a transgenic non human animal model for ulcerative colitis and its main complications such as primary sclerosing cholangitis, and colorectal cancer comprising a targeted disruption in the IL10 and NOX1 genes so that IL10 and NOX1 are not expressed in said animal.

DETAILED DESCRIPTION OF THE INVENTION

The present inventors have generated a transgenic non human animal model of ulcerative colitis. They have found that a knock-out animal for IL10 and NOX1 results in a non-human animal which naturally develops a convincing ulcerative colitis phenotype, and its complications such as primary sclerosing cholangitis and colorectal cancer phenotype. Such animals allow compounds and other therapeutic regimens to be screened and evaluated in vivo as possible treatments or preventions for ulcerative colitis, primary sclerosing cholangitis, and colorectal cancer.

Accordingly, the present invention relates to a transgenic non human animal model for ulcerative colitis and its main complications such as primary sclerosing cholangitis, and colorectal cancer comprising a targeted disruption in the IL10 and NOX1 genes so that IL10 and NOX1 are not expressed in said animal.

As used herein the term "IL10 gene" has its general meaning in the art and refers to the gene encoding for interleukin 10 (IL10)

As used herein the term "NOX1 gene" has its general meaning in the art and refers to the gene encoding for NADPH-oxidase1 (Nox1).

The term "transgene" as used herein is intended to mean a nucleic acid vector which comprises nucleotide sequences which have been manipulated in-vitro and subsequently introduced into the genome of a species such that it is stably and heritably maintained in that genome. A "transgenic animal" is an animal that contains such a transgene within its cells.

Typically, the animal is a knock-out animal for IL10 gene and NOX1 gene. A "knock-out" animal is a sub family of transgenic animals, and is an animal wherein the transgenic construct has caused an endogenous gene not to be expressed.

The transgenic non-human animal of the invention may be any animal that initially comprises an endogenous NOX1 and IL10 gene. By endogenous is meant that the gene is comprised in the genome of that animal, and would under normal circumstances be expressed to produce the corresponding protein.

Preferably, the animal is a mammal. More preferably it is a rodent, and particularly preferred is when the transgenic animal is a mouse or a rat.

In a particular embodiment, the non human animal model is obtained by cross-breeding a knock-out animal for IL10 with a knock-out animal for NOX1.

The targeted disruption may be anywhere in the genes, subject only to the requirement that it inhibits expression of functional proteins. This may be achieved, for example, by inhibiting expression of the protein completely, or by causing expression of a truncated protein, or a protein that is mutated such that it cannot perform its function, for example by engineering amino acid mutations within the active site. Typically, the targeted disruption is such that a truncated, non-functional protein is translated by using an insertion of a stop codon into an exon. The targeted disruption of the gene locus is caused by the integration into the genome of the transgenic construct. Typically, the integration is achieved by homologous recombination.

Transgenic non-human animals of the invention may be produced by methods well known in the art. There are a number of techniques that permit the introduction of genetic material, such as a transgene, into the germline. The most commonly used, and preferred protocol comprises direct injection of the transgene into the male pronucleus of the fertilised egg, resulting in the random integration into one locus of a varying number of copies, usually in a head to tail array. The injected eggs are then re-transferred into the uteri of pseudo-pregnant recipient mothers. Some of the resulting offspring may have one or several copies of the transgene integrated into their genomes, usually in one integration site. These "founder" animals are then bred to establish transgenic lines and to back-cross into the genetic background of choice. It is preferable to have the transgene insertion on both chromosomes (homozygosity) as this obviates the need for repeated genotyping in the course of routine mouse husbandry.

Alternatively, for the production of transgenic mice, transgenes can be introduced via embryonic stem (ES) cells, using electroporation, retroviral vectors or lipofection for gene transfer. This is followed by the random insertion into the genome of the pluripotent embryonic stem (ES) cells, followed by the production of chimeric mice and subsequent germline transmission. Transgenes of up to several hundred kilobases of rodentian DNA have been used to produce transgenic mice in this manner.

The transgenic animals can be subsequently tested to ensure the required genotypic change has been effected, in any suitable fashion. This can be done by, for example, detecting the presence of the transgene by PCR with specific primers, or by Southern blotting of tail DNA with a specific probe. Testing for homologous recombination leading to insertion of the transgene is done by restriction digestion. The band sizes seen if recombination has taken place are different to those seen if it has not. Suitable methods for this procedure are given in the examples. Testing for homozygosity of the transgene insertion may be carried out using quantitative Southern blotting to detect a twofold difference in signal strength between hetero- and homozygous transgenic animals. Confirmation that the gene is not being expressed can be carried out by immunohistochemical techniques.

Once the desired genotype has been confirmed the transgenic animal line can be subjected to various tests to determine the phenotype as described in the Example. The tests involved in this phenotypic characterisation depend on what genotypic change has been effected, and may include, for example, morphological, biochemical and behavioural studies.

In one embodiment, the development of a colorectal cancer may be triggered by performing an appendectomy (or a caecal floor removing) on the transgenic non human animal. The inventors have indeed demonstrated that appendectomy (or a caecal floor removing) performed on a knock-out mouse for IL10 gene and NOX1 allows the reproducible development of a spontaneous colorectal cancer at age of 4-5 weeks.

The transgenic non-human animal model of the invention may be used to screen for drugs which reverse the phenotype demonstrated, and hence may be useful in treating or preventing ulcerative colitis and its main complications such as primary sclerosing cholangitis and colorectal cancer.

Accordingly a further object of the present invention relates a method for screening a candidate compound for use as a drug for the treatment or prevention of ulcerative colitis, and/or its mains complications such as primary sclerosing cholangitis or colorectal cancer comprising i) administering a transgenic non human animal model of the invention with the candidate compound, ii) characterizing the phenotype of the non human animal model of the invention after the administration of the candidate compound and iii) positively selecting the candidate compound that reverse or delay the phenotype of the non human animal model of the invention.

The method of the invention is thus particularly suitable for identifying dugs for the treatment of ulcerative colitis and/or for identifying drugs for the treatment and prevention f the main complications of ulcerative colitis such as primary sclerosing cholangitis or colorectal cancer.

The effect of the candidate compound on the transgenic non human animal model may be evaluated by determining whether the candidate compound causes a reversal, or ameliorates in any way any of the cellular or physiological changes caused by the disease (e.g. colitis, diarrhea, high incidence of rectal bleeding, change in body and colon weights, and prolapses). Typically, the candidate compounds can be tested using the assays and tests as described in the Example.

Suitable candidate compounds which may be tested in the above methods include antibody products (for example, monoclonal and polyclonal antibodies, single chain antibodies, chimeric antibodies and CDR grafted antibodies). Furthermore, combinatorial libraries, defined chemical identities, small molecules, peptides and peptide mimetics, oligonucleotides and natural product libraries, such as display libraries (e.g. phage display libraries) may also be tested.

In a particular embodiment, the candidate compound has been previously characterized as an inhibitor of PP1R15A/GADD34 which restores eIF2α phosphorylation.

Candidate compounds positively selected in the screening methods of the invention may be used to prevent or treat ulcerative colitis, primary sclerosing cholangitis and colorectal cancer. Accordingly, condition of a patient suffering from such a disease can therefore be improved by administration of such a product. The formulation of the product for use in preventing or treating the disease will depend upon factors such as the nature of the agent identified, the precise combination of symptoms, and the severity of the disease. Typically the agent is formulated for use with a pharmaceutically acceptable carrier or diluent. For example it may be formulated for intracranial, parenteral, intravenous, intramuscular, subcutaneous, transdermal or oral administration. A physician will be able to determine the required route of administration for each particular patient. The pharmaceutical carrier or diluent may be, for example, an isotonic solution. The dose of product may be determined according to various parameters, especially according to the substance used; the age, weight and condition of the patient to be treated; the route of administration; the severity of the disease, and the required regimen. A suitable dose may however be from 0.1 to 100 mg/kg body weight such as 1 to 40 mg/kg body weight. Again, a physician will be able to determine the required route of administration and dosage for any particular patient.

The present invention also provides a kit for screening a candidate compound for use as a drug for the treatment or prevention of ulcerative colitis, primary sclerosing cholangitis and colorectal cancer, which kit comprises a non-human animal model of the invention, and means for determining whether the candidate compound can ameliorate the phenotype of the non human animal model.

The invention will be further illustrated by the following figures and examples. However, these examples and figures should not be interpreted in any way as limiting the scope of the present invention.

EXAMPLE

Ulcerative colitis (UC) is characterized by exclusive colonic involvement with superficial mucosal lesions associated with depletion in goblet cells and decreased secretion of mucins in inflammatory colonic mucosa[11]. Although it has been proposed that the epithelium of UC patients is diffusely abnormal irrespective to inflammation[12], early alterations predating inflammation within colonic epithelial cell remain elusive. It is now evident that impairment of proper ERS resolution by altered unfolded protein response (UPR) in epithelial cells can lead or sensitize to colonic inflammation both in animal[2-8] and human studies[1,2]. However, the consequences of ERS alterations during UC remain misunderstood. The UPR is a carefully orchestrated process involving three proximal sensors PERK, ATF6, and IRE1 that allow cells to cope with a wide variety of stressful conditions. The combined action of these sensors restores cell homeostasis by cessation of protein translation, increase of chaperones production, and degradation of the burden of aberrant proteins. Sustained or abnormal ERS adversely affects normal cell function leading to inflammation and/or apoptosis[13,14].

The relationship between goblet cells, ERS, and inflammation is unclear although goblet cells and mucus barrier have been linked to inflammation. However, knockout of the mucin gene Muc2 in mice is not sufficient to cause colitis since inflammation appears to arise only on a permissive genetic background[15,16] and patients with UC express MUC2. Furthermore, partial or total depletion in the number of goblet cells[17-20] and therefore in mucus and antibacterial products is insufficient to induce colitis. Finally, accumulation of missense mutated Muc2[ref.7] or HLA-27 protein[9] which is prone to misfolding in the ER, or knockout of the protein disulfide isomerase Agr2[ref.5] induce exaggerated ERS in secretory cells and subsequent inflammation. Thus, the predisposition to colitis might reside in goblet cells themselves and in their inability to manage ERS in the absence of immune dysfunction and in the setting of a normal colonic flora.

To explore the puzzling way by which goblet cells are affected by ERS in UC, we artificially increased the number of goblet cells in conditions of ERS. We crossed Nox1-deficient mice, which exhibit fine deregulation of colonic progenitor cells leading to increased goblet cell expression[10], and IL-10$^{KO}$ mice, which express deregulated ERS in epithelial intestinal cells[8] and develop enterocolitis depending on both genetic background and environmental factors[21]. The relevance of this IL-10/Nox1$^{dKO}$ model relies on the human colonic epithelial cell expression of both IL-10[22] and NOX1[23,24]. Interestingly, NOX1 expression follows the same colonic gradient than goblet cells[25] and UC lesions. Moreover, genome-wide association study demonstrate significant association of the small GTPase Rac1[ref.26] (a partner of NOX1[ref.27]) and IL-10 genes[28] with UC. Here we showed that IL-10 and NOX1 expression levels were markedly altered in uninflamed colonic mucosa from patients with UC (n=12) versus healthy controls (n=12).

All SPF-reared C57B1/6-IL10/Nox1$^{dKO}$ mice developed spontaneously colitis at 67 weeks and disease activity index (DAI) scores which became more severe with age, including diarrhea, high incidence of rectal bleeding, change in body and colon weights, and prolapses. None of WT and single-KO mice developed colitis during the time frame studied. Histopathologic scores revealed that IL10/Nox1$^{dKO}$ mice developed more severe colitis along the proximal-distal axis and exhibited signs of UC without any signs of ileitis including polymorphonuclear infiltrates, crypt abscesses, edema, focal epithelial erosion, and crypt loss. We next measured epithelial permeability of FITC-dextran in segments of distal colon and indigenous bacterial translocation was identified in the spleen of 7 and 12-week-old mice. Consistent with the colitis state, only IL10/Nox1$^{dKO}$ mice demonstrated an increased permeability in the colon and exhibited splenomegaly which was closely correlated with increased Gram-negative commensal bacteria translocation. Interestingly, IL10/Nox1$^{dKO}$ mice showed the main complications of UC such as colitis-associated colorectal cancer and spontaneously primary sclerosing cholangitis at 7/8 months of age. By contrast, IL10$^{dKO}$ mice showed mild enterocolitis at low frequency (<20% at 34 weeks), without showing any signs of cholangitis or colorectal cancer (at >8 months of age; this study and[29]). Interestingly, here we report the comprehensive genome-wide screen of 561 microRNAs of colonic epithelial mucosa of Nox1$^{KO}$, IL10$^{KO}$, and IL10/Nox1$^{dKO}$ mice (6- and 16-wk-old) versus WT mice. Consistent with previous findings in patients with UC[30,31], IL10/Nox1$^{dKO}$ mice expressed almost 50% of microRNAs relevant in defining UC signature.

To analyze cytokine responses at the site of inflammation, colon samples were collected and various cytokines were analyzed at both mRNA and protein levels. IL10/Nox1$^{dKO}$ mice showed increased expression levels of pro-inflammatory cytokines mainly involved in UC. Lymphoid and myeloid cell population analysis in the spleen did not differ between the four genotypes. By contrast, a massive infiltration of FoxP3$^+$ T$_{reg}$ was only observed in the colonic tissue in spite of active mucosal inflammation and at lesser extent in the spleen of IL10/Nox1$^{dKO}$ mice consistent with findings in UC[32]. To determine whether the genotype of hematopoietic lineages affected the extent of colitis, we generated bone marrow (BM) chimeric mice in which recipients and donors were WT (CD45.1) and WT, IL10$^{KO}$, and IL10/Nox1$^{dKO}$ mice (CD45.2), respectively. Interestingly, reconstitution of irradiated WT mice with IL10$^{KO}$ or IL10/Nox1$^{dKO}$ BM was insufficient to cause disease demonstrating that colitis is chiefly inherent to epithelial cells rather than hematopoietic lineages in IL10/Nox1$^{dKO}$ mice.

The colonic epithelium of IL10/Nox1$^{dKO}$ mice showed a paucity of Alcian Blue/PAS positive mucins associated with loss of goblet cells at the ulcerated sites. Accordingly, Muc2 and Muc4 protein expression levels were dramatically low in the inflamed colonic areas of IL10/Nox1$^{dKO}$ mice. Rarefaction and aberrant morphology of goblet cells with few and immature thecae associated with small amount of mucus and swollen, round mitochondria were similarly observed in the colon of both IL10/Nox1$^{dKO}$ mice and patients with UC.

Colonic section of IL10/Nox1$^{dKO}$ mice displayed an increase in the number of PCNA- and phospho-histone 3-positive cells suggesting increased epithelial proliferation. Scanning electron microscopy (SEM) showed a ~30% increase in crypt length in IL10/Nox1$^{dKO}$ mice. Interestingly, SEM displayed a wide spectrum of identical ultrastructural alterations of the mucosa both in IL10/Nox1$^{dKO}$ mice and in unaffected colonic mucosa of patients with UC including crypt distortion, visible crypt openings disposed in rows, edematous glandular borders, and dilatation of the gland lumen. Notwithstanding increased colonic proliferation, staining and quantitative assessment of apoptotic cells indicated that decreased expression of goblet cells in IL10/Nox1$^{dKO}$ mice was due to increased apoptosis in the colon.

To assess the pathogenic role of goblet cells in UC, WT and Nox1$^{KO}$ mice were subjected to oral administration of DSS or rectal administration of TNBS. No significant differences in DAI and histological damages of colonic mucosa were seen between the two mouse models suggesting that chemically-induced inflammation is likely independent of increased expression of goblet cells. By contrast, tunicamycin treatment, a canonical inducer of ERS, significantly induced a more severe colitis in mice overexpressing goblet cells than in WT mice indicating that goblet cell itself may be a direct participant in the development of colitis as a consequence of ERS. Accordingly, IL10/Nox1$^{dKO}$ mice exhibited ERS disturbances in the colonic mucosa prior inflammatory damages as previously described in patients with UC[1]. IRE1beta and ATF6alpha branch signaling were extended in colonic epithelial cells as evidenced by the increased XBP-1 mRNA splicing, the induction of GRP78, GRP94, PDI at both mRNA and protein levels, and dilated cisternae and gross distortion of the ER in goblet cells. Interestingly, identical defective phosphorylation of eIF2α correlated with low expression of ATF4 was observed both in unaffected colonic mucosa of IL10/Nox1$^{dKO}$ mice and patients with UC[1]. Consistent with reduced eIF2α phosphorylation, increased expression of PPP1R15A/GADD34, a stress-inducible protein that recruits the catalytic subunit of protein phosphatase 1 and promotes eIF2alpha dephosphorylation, was detected in agreement with our previous data in humans[1]. EIF2alpha phosphorylation is cytoprotective during ERS, because cells are sensitized to cell death when this pathway is genetically ablated[33] and protected when it is ectopically enforced[34]. To test whether a selective pharmacological inhibitor of GADD34-mediated eIF2alpha dephosphorylation may alleviate colitis, IL10/Nox1$^{dKO}$ mice were treated with 1 mg/kg salubrinal[35] for up to three weeks. We showed that salubrinal strongly reduced histological colitis score throughout the colon, markedly prevented immune cell infiltration, and restored intact mucosal architecture with normal goblet cells. Salubrinal caused robust eIF2alpha phosphorylation and protected colonic mucosa against apoptosis at least in part for its anti-apoptotic activity on CHOP expression. Furthermore, there was a trend toward reduced Grp78/Bip and Grp94 expression in salubrinal-treated mice demonstrating that salubrinal engages the translational control arm of the UPR by inducing eIF2alpha phosphorylation and acts like a proteostasis regulator by lowering protein folding in stressed cells. Interestingly, we demonstrated that salubrinal-induced phosphorylation of eIF2alpha was mainly detected in colonic epithelial cells. Finally, levels of proinflammatory cytokines and amount of colonic and splenic $T_{reg}$ cells were strongly decreased to baseline in salubrinal-treated IL10/Nox1$^{dKO}$ mice.

Our findings strengthen that defective eIF2alpha phosphorylation is a major player in UC and may open new therapeutic avenues. Current treatments of UC cannot change the natural course of the disease. These difficulties to manage UC may be explained by the use of immunomodulators which are mainly designed to modulate the activity of immune cells and are hardly efficient to repair early epithelial abnormalities. Thus, eIF2α modulators could define a new class of drugs specifically based on the intimate mechanisms of UC which might likely shift the paradigm for UC treatment from immunomulators to epitheliomodulators.

References:

Throughout this application, various references describe the state of the art to which this invention pertains. The disclosures of these references are hereby incorporated by reference into the present disclosure.

1. Treton, X., et al. Altered endoplasmic reticulum stress affects translation in inactive colon tissue from patients with ulcerative colitis. *Gastroenterology* 141, 1024-1035 (2011).
2. Kaser, A., et al. XBP1 links ER stress to intestinal inflammation and confers genetic risk for human inflammatory bowel disease. *Cell* 134, 743-756 (2008).
3. Bertolotti, A., et al. Increased sensitivity to dextran sodium sulfate colitis in IRE1beta-deficient mice. *J Clin Invest* 107, 585-593 (2001).
4. Brandl, K., et al. Enhanced sensitivity to DSS colitis caused by a hypomorphic Mbtps1 mutation disrupting the ATF6-driven unfolded protein response. *Proc Natl Acad Sci USA* 106, 3300-3305 (2009).
5. Zhao, F., et al. Disruption of Paneth and goblet cell homeostasis and increased endoplasmic reticulum stress in Agr2-/- mice. *Dev Biol* 338, 270-279 (2009).
6. Cao, S. S., Song, B. & Kaufman, R. J. PKR protects colonic epithelium against colitis through the unfolded protein response and prosurvival signaling. *Inflamm Bowel Dis* (2012).
7. Heazlewood, C. K., et al. Aberrant mucin assembly in mice causes endoplasmic reticulum stress and spontaneous inflammation resembling ulcerative colitis. *PLoS Med* 5, e54 (2008).
8. Shkoda, A., et al. Interleukin-10 blocked endoplasmic reticulum stress in intestinal epithelial cells: impact on chronic inflammation. *Gastroenterology* 132, 190-207 (2007).
9. Turner, M. J., et al. HLA-B27 misfolding in transgenic rats is associated with activation of the unfolded protein response. *J Immunol* 175, 2438-2448 (2005).
10. Coant, N., et al. NADPH oxidase 1 modulates WNT and NOTCH1 signaling to control the fate of proliferative progenitor cells in the colon. *Mol Cell Biol* 30, 2636-2650 (2010).
11. Tytgat, K. M., van der Wal, J. W., Einerhand, A. W., Buller, H. A. & Dekker, J. Quantitative analysis of MUC2 synthesis in ulcerative colitis. *Biochem Biophys Res Commun* 224, 397-405 (1996).
12. Gibson, P., Rosella, O., Nov, R. & Young, G. Colonic epithelium is diffusely abnormal in ulcerative colitis and colorectal cancer. *Gut* 36, 857-863 (1995).
13. Ron, D. & Walter, P. Signal integration in the endoplasmic reticulum unfolded protein response. *Nat Rev Mol Cell Biol* 8, 519-529 (2007).
14. Zhang, K. & Kaufman, R. J. From endoplasmic-reticulum stress to the inflammatory response. *Nature* 454, 455-462 (2008).
15. Van der Sluis, M., et al. Muc2-deficient mice spontaneously develop colitis, indicating that MUC2 is critical for colonic protection. *Gastroenterology* 131, 117-129 (2006).
16. Velcich, A., et al. Colorectal cancer in mice genetically deficient in the mucin Muc2. *Science* 295, 1726-1729 (2002).
17. Gregorieff, A., et al. The ets-domain transcription factor Spdef promotes maturation of goblet and paneth cells in the intestinal epithelium. *Gastroenterology* 137, 1333-1345 e1331-1333 (2009).
18. Itoh, H., Beck, P. L., Inoue, N., Xavier, R. & Podolsky, D. K. A paradoxical reduction in susceptibility to colonic injury upon targeted transgenic ablation of goblet cells. *J Clin Invest* 104, 1539-1547 (1999).
19. Shroyer, N. F., Wallis, D., Venken, K. J., Bellen, H. J. & Zoghbi, H. Y. Gfi1 functions downstream of Math1 to control intestinal secretory cell subtype allocation and differentiation. *Genes Dev* 19, 2412-2417 (2005).
20. Yang, Q., Bermingham, N. A., Finegold, M. J. & Zoghbi, H. Y. Requirement of Math1 for secretory cell lineage commitment in the mouse intestine. *Science* 294, 2155-2158 (2001).
21. Kuhn, R., Lohler, J., Rennick, D., Rajewsky, K. & Muller, W. Interleukin-10-deficient mice develop chronic enterocolitis. *Cell* 75, 263-274 (1993).
22. Jarry, A., et al. Mucosal IL-10 and TGF-beta play crucial roles in preventing LPS-driven, IFN-gamma-mediated epithelial damage in human colon explants. *J Clin Invest* 118, 1132-1142 (2008).
23. Kamizato, M., et al. Interleukin 10 inhibits interferon gamma- and tumor necrosis factor alpha-stimulated activation of NADPH oxidase 1 in human colonic epithelial cells and the mouse colon. *J Gastroenterol* 44, 1172-1184 (2009).
24. Valente, A. J., et al. Regulation of NOX1 expression by GATA, HNF-1alpha, and Cdx transcription factors. *Free Radic Biol Med* 44, 430-443 (2008).
25. Szanto, I., et al. Expression of NOX1, a superoxide-generating NADPH oxidase, in colon cancer and inflammatory bowel disease. *J Pathol* 207, 164-176 (2005).
26. Muise, A. M., et al. Single nucleotide polymorphisms that increase expression of the guanosine triphosphatase RAC1 are associated with ulcerative colitis. *Gastroenterology* 141, 633-641 (2011).
27. Cheng, G., Diebold, B. A., Hughes, Y. & Lambeth, J. D. Nox1-dependent reactive oxygen generation is regulated by Rac1. *J Biol Chem* 281, 17718-17726 (2006).
28. Franke, A., et al. Sequence variants in IL10, ARPC2 and multiple other loci contribute to ulcerative colitis susceptibility. *Nat Genet* 40, 1319-1323 (2008).

29. Kanneganti, M., Mino-Kenudson, M. & Mizoguchi, E. Animal models of colitis-associated carcinogenesis. *J Biomed Biotechnol* 2011, 342637 (2011).

30. Fasseu, M., et al. Identification of restricted subsets of mature microRNA abnormally expressed in inactive colonic mucosa of patients with inflammatory bowel disease. *PLoS One* 5(2010).

31. Pekow, J. R. & Kwon, J. H. MicroRNAs in inflammatory bowel disease. *Inflamm Bowel Dis* 18, 187-193 (2011).

32. Yu, Q. T., et al. Expression and functional characterization of FOXP3+ CD4+ regulatory T cells in ulcerative colitis. *Inflamm Bowel Dis* 13, 191-199 (2007).

33. Scheuner, D., et al. Translational control is required for the unfolded protein response and in vivo glucose homeostasis. *Mol Cell* 7, 1165-1176 (2001).

34. Jousse, C., et al. Inhibition of a constitutive translation initiation factor 2alpha phosphatase, CReP, promotes survival of stressed cells. *J Cell Biol* 163, 767-775 (2003).

35. Boyce, M., et al. A selective inhibitor of eIF2alpha dephosphorylation protects cells from ER stress. *Science* 307, 935-939 (2005).

36. Ruimy, R., et al. Phylogenetic analysis and assessment of the genera Vibrio, Photobacterium, Aeromonas, and Plesiomonas deduced from small-subunit rRNA sequences. *Int J Syst Bacteriol* 44, 416-426 (1994).

The invention claimed is:

1. A method for screening a candidate compound for use as a drug for the treatment or prevention of ulcerative colitis and/or complications thereof comprising i) administering the candidate compound to a transgenic non human animal model comprising a targeted disruption in the Interleukin 10 (IL10) and NADPH-oxidase1 (NOX1) genes so that IL10 and NOX1 are not expressed in said animal, ii) characterizing the phenotype of the non human animal model after the administration of the candidate compound and iii) positively selecting the candidate compound that reverses or delays the ulcerative colitis phenotype of the non human animal model and identifying it as candidate compound for use as a drug for the treatment or prevention of ulcerative colitis and/or its main complications.

2. A method for screening a candidate compound for use as a drug for the treatment or prevention of ulcerative colitis and/or complications thereof comprising i) administering the candidate compound to a transgenic non human animal model comprising a targeted disruption in the Interleukin 10 (IL10) and NADPH-oxidase1 (NOX1) genes so that IL10 and NOX1 are not expressed in said animal, ii) characterizing the phenotype of the non human animal model after the administration of the candidate compound and iii) positively selecting the candidate compound that reverses or delays the ulcerative colitis phenotype of the non human animal model and identifying it as candidate compound for use as a drug for the treatment or prevention of ulcerative colitis and/or complications thereof wherein the candidate compound has been previously characterized as an inhibitor of PP1R15A/GADD34 which restores eIF2α phosphorylation.

3. The method of claim 1, wherein said complications include primary sclerosing cholangitis and colorectal cancer.

4. The method of claim 1, wherein the transgenic non human animal model is a knock-out for IL-10 and NOX 1.

5. The method of claim 1, wherein the transgenic non human animal model is a rodent.

6. The method of claim 1, further comprising the step of performing an appendectomy or a caecal floor removing on the transgenic non human animal model.

* * * * *